US008492616B2

(12) United States Patent
Mero

(10) Patent No.: US 8,492,616 B2
(45) Date of Patent: Jul. 23, 2013

(54) BROCCOLI HYBRID PS05151639

(75) Inventor: Carl E. Mero, Arroyo Grande, CA (US)

(73) Assignee: Seminis Vegetable Seeds, Inc., Woodland, CA (US)

(*) Notice: Subject to any disclaimer, the term of this patent is extended or adjusted under 35 U.S.C. 154(b) by 276 days.

(21) Appl. No.: 12/859,034

(22) Filed: Aug. 18, 2010

(65) Prior Publication Data
US 2011/0055945 A1 Mar. 3, 2011

Related U.S. Application Data

(60) Provisional application No. 61/238,602, filed on Aug. 31, 2009.

(51) Int. Cl.
A01H 5/00 (2006.01)
A01H 5/10 (2006.01)
A01H 1/00 (2006.01)
C12N 15/82 (2006.01)

(52) U.S. Cl.
USPC ............................ 800/306; 800/260; 435/430

(58) Field of Classification Search
None
See application file for complete search history.

(56) References Cited

U.S. PATENT DOCUMENTS 6,340,784 B1    1/2002  Mithen et al.
7,829,763 B2 * 11/2010  Barham et al. ................ 800/306

FOREIGN PATENT DOCUMENTS

EP  1 069 819 B1   7/2002
EP  1069819 B1     7/2002

OTHER PUBLICATIONS

Jun. 30, 2011 Information Disclosure Statement for U.S. Appl. No. 12/859,034.
Falukner et al., Increase of Anticarcinogenic Glucosinolates in Brassica oleracea L. Italica (broccoli), ISHS Symposium on Brassicas, Tenth Crucifer Genetics Workshop, Book of Abstracts, pp. 237, Rennes, France, Sep. 23-27, 1997. (abstract).
Faulkner et al., "Selective increase of the potential anticarcinogen 4-methylsulphinylbutyl glucosinolate in broccoli", Carcinogenesis, 19(4):605-609, 1998.
Giamoustaris et al., "Genetics of aliphatic glucosinolates. IV. Side-chain modification in Brassica oleracea", Theor Appl Genet, 93:1006-1010, 1996.
Hansen et al., "Glucosinolates in broccoli stored under controlled atmosphere," J. Amer. Soc. Hort. Sci., 120(6):1069-1074, 1995.
Mithen et al., "Development of isothiocyanate-enriched broccoli, and its enhanced ability to induce phase 2 detoxification enzymes in mammalian cells", Theor. Appl. Genet., 106:727-734, 2003.
Mithen et al., "Glucosinolates of wild and cultivated Brassica species", Phytochemistry, 26(7):1969-1973, 1987.
Rosa et al., "Changes in glucosinolate concentrations in Brassica crops (B oleracea and B napus) throughout growing seasons", J Sci Food Agric, 71:237-244, 1996.
U.S. Appl. No. 61/572,271, filed Jun. 15, 2011, Mero.
Faulkner, Kathy et. al., Increases of Anticarcinogenic Glucosinolates in Brassicat Oleracea L. Italica (Broccoli), ISHS Synposium on Brassicas—Tenth Crucifer Genetics Workshops—Book of Abstracts, Sep. 23-27, 1997, p. 237, International Societe for Horticultural Science Crucifer Gentetics Cooperative, Institut National de la Recherche Agronomique Ecole Nationale Superieure Agronomique de Rennes, Rennes, France.
Giamoustaris, A. et. al., Genetics of aliphatic glucosinolates. IV. Side-chain modification in Brassica oleracea, Theoretical and Applied. Genetics., 1996, pp. 1006-1010, vol. 93, Springer-Verlag, Stuttgart, Germany.
Rosa, Eduardo A. S. et. al., Changes in Glucosinolate Concentrations in Brassica Crops (B oleracea and B napus) Throughout Growing Seasons, Journal of the Science of Food and Agiculture, 1996, pp. 237-244, vol. 71, Society of Chemical Industry, London, United Kingdom.
Mithen, Richard F. et. al., Glucosinates of wild and cultivated Brassica Species, Phytochemistry, 1987, pp. 1969-1973, vol. 26, No. 7, Elsevier, Amsterdam, The Netherlands.

* cited by examiner

Primary Examiner — Elizabeth McElwain
(74) Attorney, Agent, or Firm — Dentons US LLP; Alissa Eagle, Esq.

(57) ABSTRACT

The invention provides seed and plants of broccoli hybrid PS05151639 and the parent lines thereof. The invention thus relates to the plants, seeds and tissue cultures of broccoli hybrid PS05151639 and the parent lines thereof, and to methods for producing a broccoli plant produced by crossing such plants with themselves or with another broccoli plant, such as a plant of another genotype. The invention further relates to seeds and plants produced by such crossing. The invention further relates to parts of such plants.

35 Claims, 11 Drawing Sheets

US 8,492,616 B2

BROCCOLI HYBRID PS05151639

CROSS-REFERENCE TO RELATED APPLICATIONS

This application claims the priority of U.S. Provisional Appl. Ser. No. 61/238,602, filed Aug. 31, 2009, the entire disclosure of which is incorporated herein by reference.

FIELD OF THE INVENTION

The present invention relates to the field of plant breeding and, more specifically, to the development of broccoli hybrid PS05151639 and the parent broccoli lines BRM 51-1162 and BRL 51-1128.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a broccoli plant of the hybrid designated PS05151639. Also provided are broccoli plants having all the physiological and morphological characteristics of broccoli hybrid PS05151639 and/or broccoli lines BRM 51-1162 and BRL 51-1128. Parts of a broccoli plant of the present invention are also provided, for example, including pollen, an ovule, a floret, a head, and a cell of the plant.

In another aspect of the invention, a plant of broccoli hybrid PS05151639 and/or broccoli lines BRM 51-1162 and BRL 51-1128 comprising an added heritable trait is provided. The heritable trait may comprise a genetic locus that is, for example, a dominant or recessive allele. In one embodiment of the invention, a plant of broccoli hybrid PS05151639 and/or broccoli lines BRM 51-1162 and BRL 51-1128 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of broccoli hybrid PS05151639 and/or broccoli lines BRM 51-1162 and BRL 51-1128. The broccoli seed of the invention may, in one embodiment, be provided as an essentially homogeneous population of broccoli seed of broccoli hybrid PS05151639 and/or broccoli lines BRM 51-1162 and BRL 51-1128. Essentially homogeneous populations of seed are generally free from substantial numbers of other seed. Therefore, seed of hybrid PS05151639 and/or broccoli lines BRM 51-1162 and BRL 51-1128 may be defined, in one non-limiting embodiment, as forming at least about 97% of the total seed, including at least about 98%, 99% or more of the seed. The seed population can be separately grown to provide an essentially homogeneous population of broccoli plants designated PS05151639 and/or broccoli lines BRM 51-1162 and BRL 51-1128.

In yet another aspect of the invention, a tissue culture of regenerable cells of a broccoli plant of hybrid PS05151639 and/or broccoli lines BRM 51-1162 and BRL 51-1128 is provided. The tissue culture will preferably be capable of regenerating broccoli plants capable of expressing all of the physiological and morphological characteristics of the starting plant, and of regenerating plants having substantially the same genotype as the starting plant. Examples of some of the physiological and morphological characteristics of the hybrid PS05151639 and/or broccoli lines BRM 51-1162 and BRL 51-1128 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides broccoli plants regenerated from a tissue culture of the invention, the plants having all the physiological and morphological characteristics of hybrid PS05151639 and/or broccoli lines BRM 51-1162 and BRL 51-1128.

In still yet another aspect, the invention provides a broccoli floret comprising an endogenous content of MSB (glucoraphanin) and MSP (glucoiberin) present in a ratio of MSB to MSP of from about 2:1 to about 40:1 on a weight to weight basis. In particular embodiments of the invention, the ratio is at least about 2:1, 3:1, 4:1, 5:1, 6:1, 8:1 or 10:1. In further embodiments, the ratio may from about 2:1 to about 30:1, from about 2:1 to about 20:1, from about 2:1 to about 15:1, from about 2:1 to about 10:1, from about 2:1 to about 8:1, from about 2:1 to about 6:1, from about 3:1 to about 25:1, from about 3:1 to about 20:1, from about 3:1 to about 15:1, from about 3:1 to about 10:1, from about 3:1 to about 7:1, from about 4:1 to about 30:1, from about 4:1 to about 20:1, from about 4:1 to about 15:1, from about 4:1 to about 10:1, from about 5:1 to about 30:1, from about 5:1 to about 15:1, or from about 5:1 to about 10:1. In one embodiment the floret contains at least about 10 μmole/g dry weight MSB and MSP. In specific embodiments, the floret may contain about 10 μmole, 15 μmole, 20 μmole, 25 μmole, 30 μmole, 40 μmole, 50 μmole, 60 μmole, 70 μmole, 80 μmole, 90 μmole, 100 μmole, 125 μmole, 150 μmole or more MSB and/or MSP. In specific embodiments, the floret is obtained from a hybrid broccoli plant. In one embodiment, the floret is obtained from a broccoli plant adapted for commercial cultivation. By "adapted for commercial product" it is meant that a plant is of a variety that has been bred to be suitable for cultivation. As is known in the art of plant breeding, such plants have a culmination of distinguishable traits such as vigor, disease or stress resistance, and yield that allows a producer to harvest a product of commercial significance. Also provided by the invention is a broccoli plant that produces such florets.

In still yet another aspect of the invention, processes are provided for producing broccoli seeds, plants and parts thereof, which processes generally comprise crossing a first parent broccoli plant with a second parent broccoli plant, wherein at least one of the first or second parent broccoli plants is a plant of broccoli line BRM 51-1162 or broccoli line BRL 51-1128. These processes may be further exemplified as processes for preparing hybrid broccoli seed or plants, wherein a first broccoli plant is crossed with a second broccoli plant of a different, distinct genotype to provide a hybrid that has, as one of its parents, a plant of broccoli line BRM 51-1162 or broccoli line BRL 51-1128. In these processes, crossing will result in the production of seed. The seed production occurs regardless of whether the seed is collected or not.

In one embodiment of the invention, the first step in "crossing" comprises planting seeds of a first and second parent broccoli plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent broccoli plants into plants that bear flowers. A third step may comprise preventing self-pollination of the plants, such as by emasculating the flowers (i.e., killing or removing the pollen).

A fourth step for a hybrid cross may comprise cross-pollination between the first and second parent broccoli plants. Yet another step comprises harvesting the seeds from at least one of the parent broccoli plants. The harvested seed can be grown to produce a broccoli plant or hybrid broccoli plant.

The present invention also provides the broccoli seeds and plants produced by a process that comprises crossing a first parent broccoli plant with a second parent broccoli plant, wherein at least one of the first or second parent broccoli plants is a plant of broccoli hybrid PS05151639 and/or broccoli lines BRM 51-1162 and BRL 51-1128. In one embodiment of the invention, broccoli seed and plants produced by the process are first generation ($F_1$) hybrid broccoli seed and plants produced by crossing a plant in accordance with the invention with another, distinct plant. The present invention further contemplates plant parts of such an $F_1$ hybrid broccoli plant, and methods of use thereof. Therefore, certain exemplary embodiments of the invention provide an $F_1$ hybrid broccoli plant and seed thereof.

In still yet another aspect, the present invention provides a method of producing a plant derived from hybrid PS05151639 and/or broccoli lines BRM 51-1162 and BRL 51-1128, the method comprising the steps of: (a) preparing a progeny plant derived from hybrid PS05151639 and/or broccoli lines BRM 51-1162 and BRL 51-1128, wherein said preparing comprises crossing a plant of the hybrid PS05151639 and/or broccoli lines BRM 51-1162 and BRL 51-1128 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid PS05151639 and/or broccoli lines BRM 51-1162 and BRL 51-1128. The plant derived from hybrid PS05151639 and/or broccoli lines BRM 51-1162 and BRL 51-1128 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid PS05151639 and/or broccoli lines BRM 51-1162 and BRL 51-1128 is obtained which possesses some of the desirable traits of the line/hybrid as well as potentially other selected traits.

In certain embodiments, the present invention provides a method of producing food or feed comprising: (a) obtaining a plant of broccoli hybrid PS05151639 and/or broccoli lines BRM 51-1162 and BRL 51-1128, wherein the plant has been cultivated to maturity, and (b) collecting tissue of the plant.

In still yet another aspect of the invention, the genetic complement of broccoli hybrid PS05151639 and/or broccoli lines BRM 51-1162 and BRL 51-1128 is provided. The phrase "genetic complement" is used to refer to the aggregate of nucleotide sequences, the expression of which sequences defines the phenotype of, in the present case, a broccoli plant, or a cell or tissue of that plant. A genetic complement thus represents the genetic makeup of a cell, tissue or plant, and a hybrid genetic complement represents the genetic make up of a hybrid cell, tissue or plant. The invention thus provides broccoli plant cells that have a genetic complement in accordance with the broccoli plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid PS05151639 and/or broccoli lines BRM 51-1162 and BRL 51-1128 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by broccoli plant cells, tissues, plants, and seeds, formed by the combination of a haploid genetic complement of a broccoli plant of the invention with a haploid genetic complement of a second broccoli plant, preferably, another, distinct broccoli plant. In another aspect, the present invention provides a broccoli plant regenerated from a tissue culture that comprises a hybrid genetic complement of this invention.

In still yet another aspect, the invention provides a broccoli line BRM 51-1162 that exhibits a combination of traits comprising stable transmission of commercially useful traits and an elevated level of the phytochemicals MSP (glucoiberin). In certain embodiments, the combination of traits may be defined as controlled by genetic means for the expression of the combination of traits found in broccoli line BRM 51-1162.

In still yet another aspect, the invention provides a hybrid broccoli plant that exhibits a combination of traits comprising superior commercial traits combined with increased levels of the phytochemical MSB (glucoraphanin) and MSP (glucoiberin) (see, e.g., FIGS. 1-11 and Tables 5-6). In certain embodiments, the combination of traits may be defined as controlled by genetic means for the expression of the combination of traits found in broccoli hybrid PS05151639.

In still yet another aspect, the invention provides a method of determining the genotype of a plant of broccoli hybrid PS05151639 and/or broccoli lines BRM 51-1162 and BRL 51-1128 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
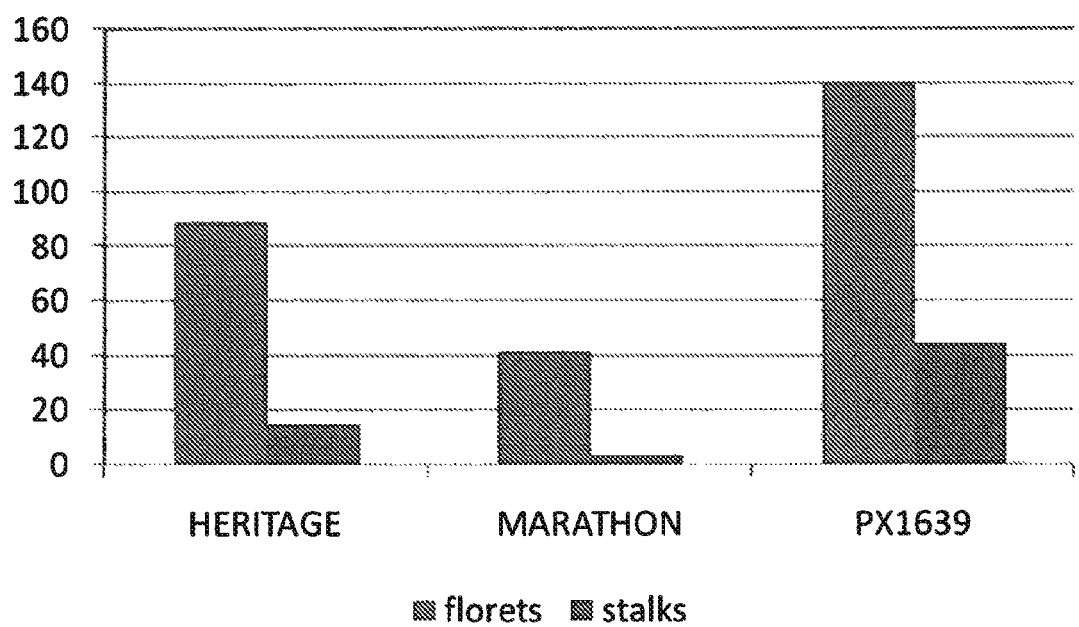
FIG. 1 shows MSB levels expressed in mg/148 g of starting material for hybrid PS05151639 (labeled "PX1639") and two comparison varieties. MSB was quantified in stalks and florets by standard methods.
Figure 2:
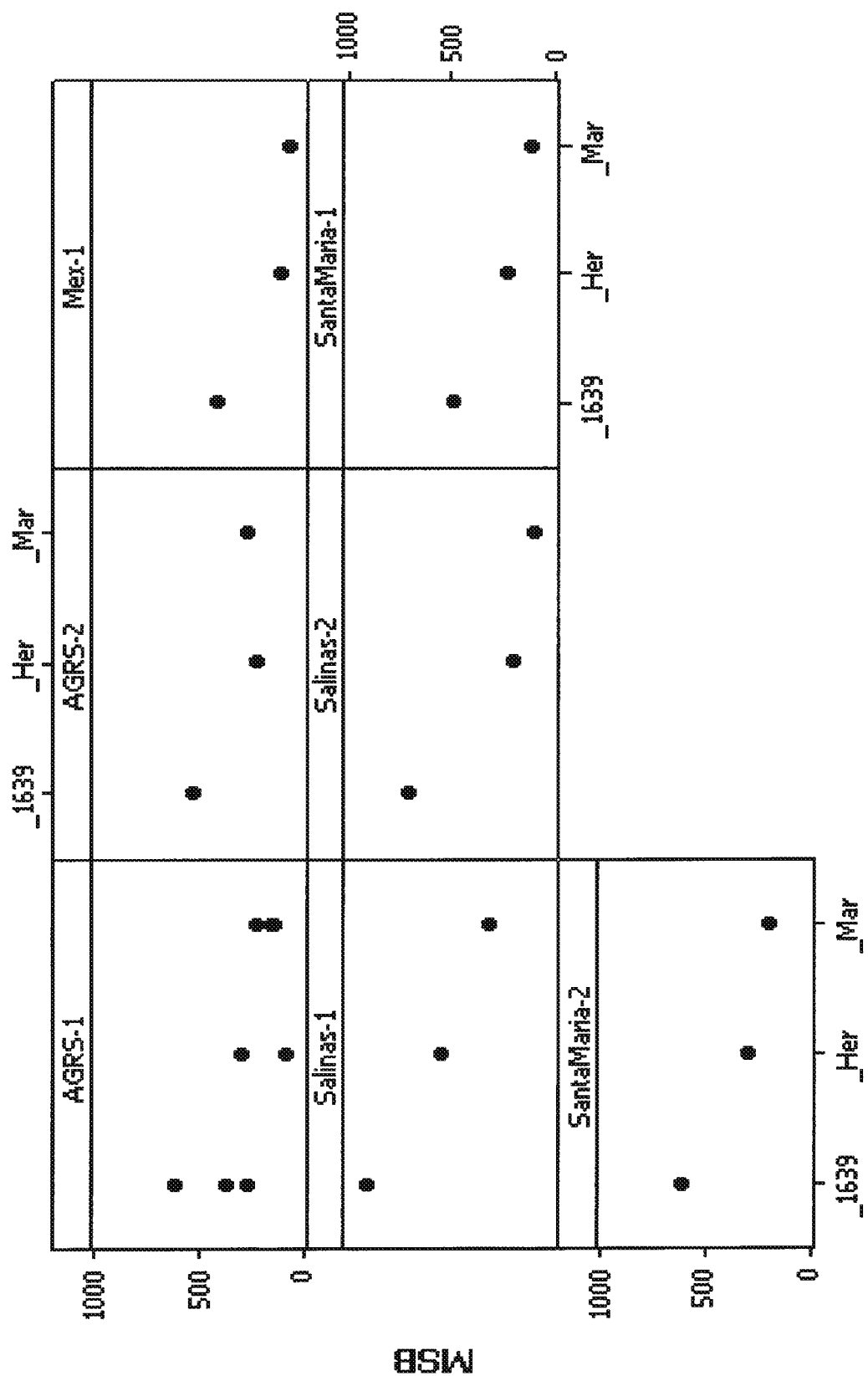
FIG. 2 shows MSB levels in PS05151639 ("1639") and two comparison varieties grown at five different locations in one growing season. Trials were conducted in RCB with 3-4 replicates per variety or in strip plots, unreplicated within a location. MSB was quantified by standard methods.
Figure 3:
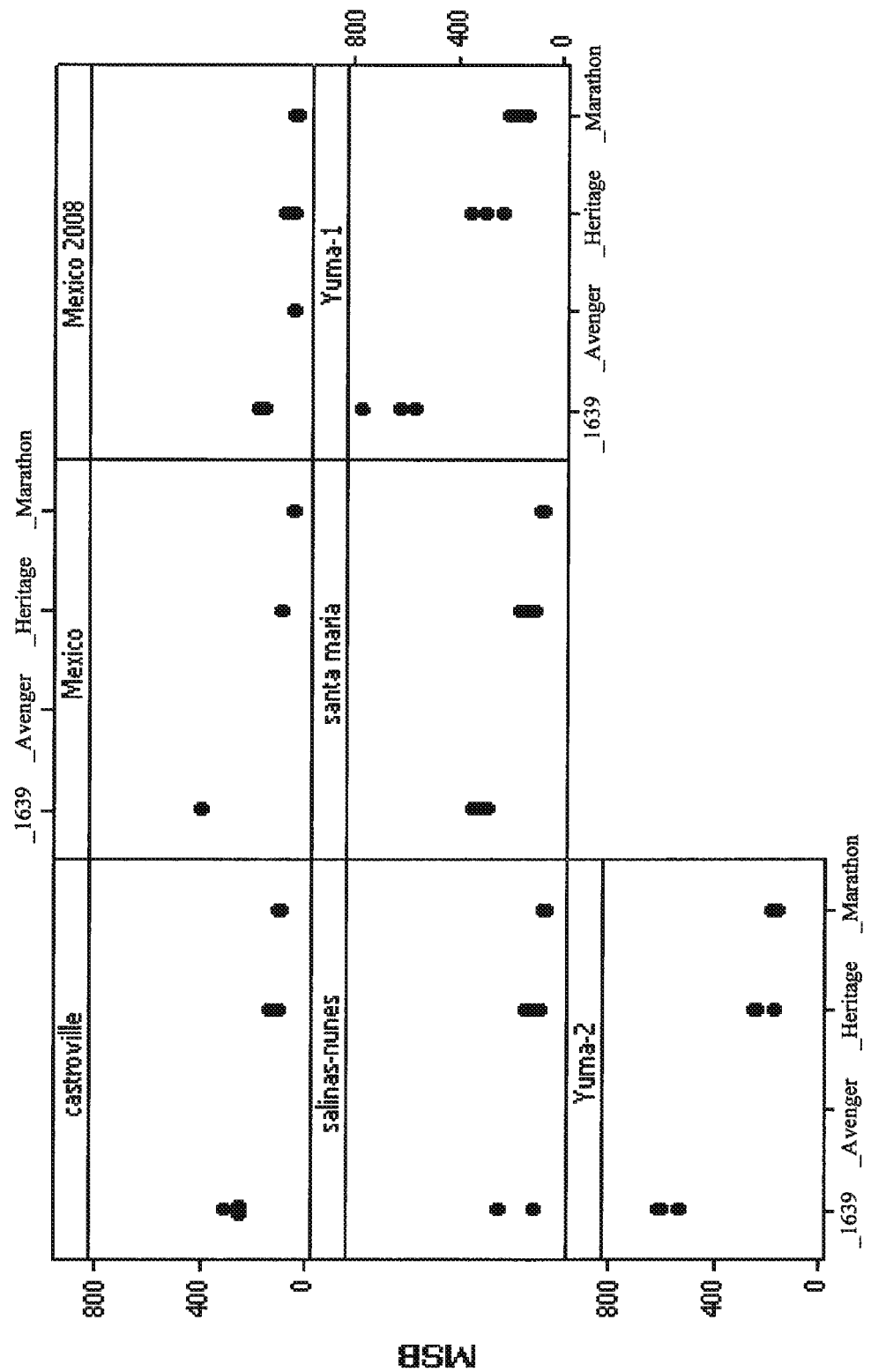
FIG. 3 shows MSB levels in PS05151639 ("1639") and two comparison varieties grown at five different locations in one growing season. Trials were conducted in RCB with 3-4 replicates per variety or in strip plots, unreplicated within a location. MSB was quantified by standard methods.
Figure 4:
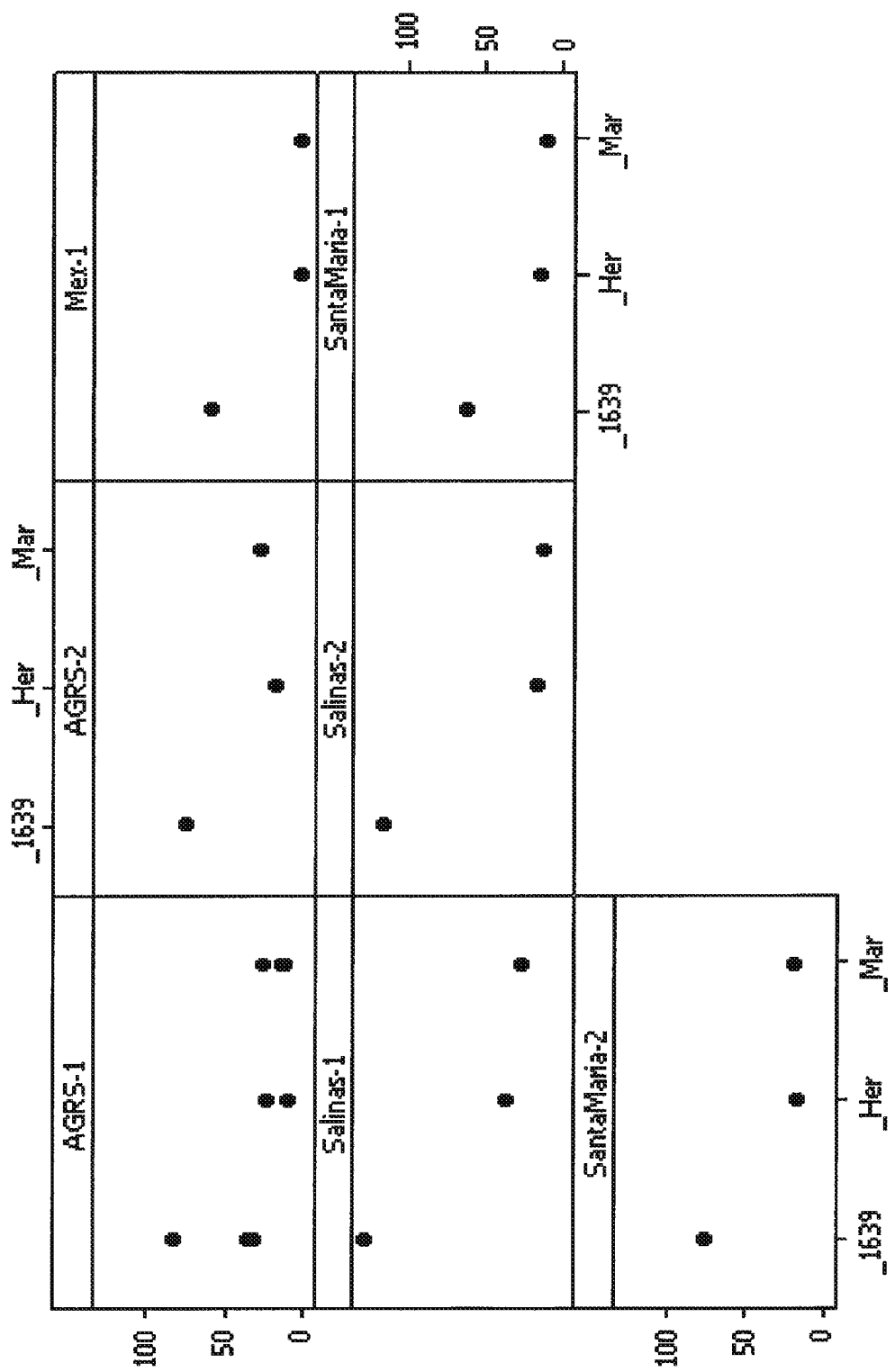
FIG. 4 shows MSP levels in PS05151639 ("1639") and two comparison varieties grown at five different locations in one growing season. Trials were conducted in RCB with 3-4 replicates per variety or in strip plots, unreplicated within a location. MSP was quantified by standard methods.
Figure 5:
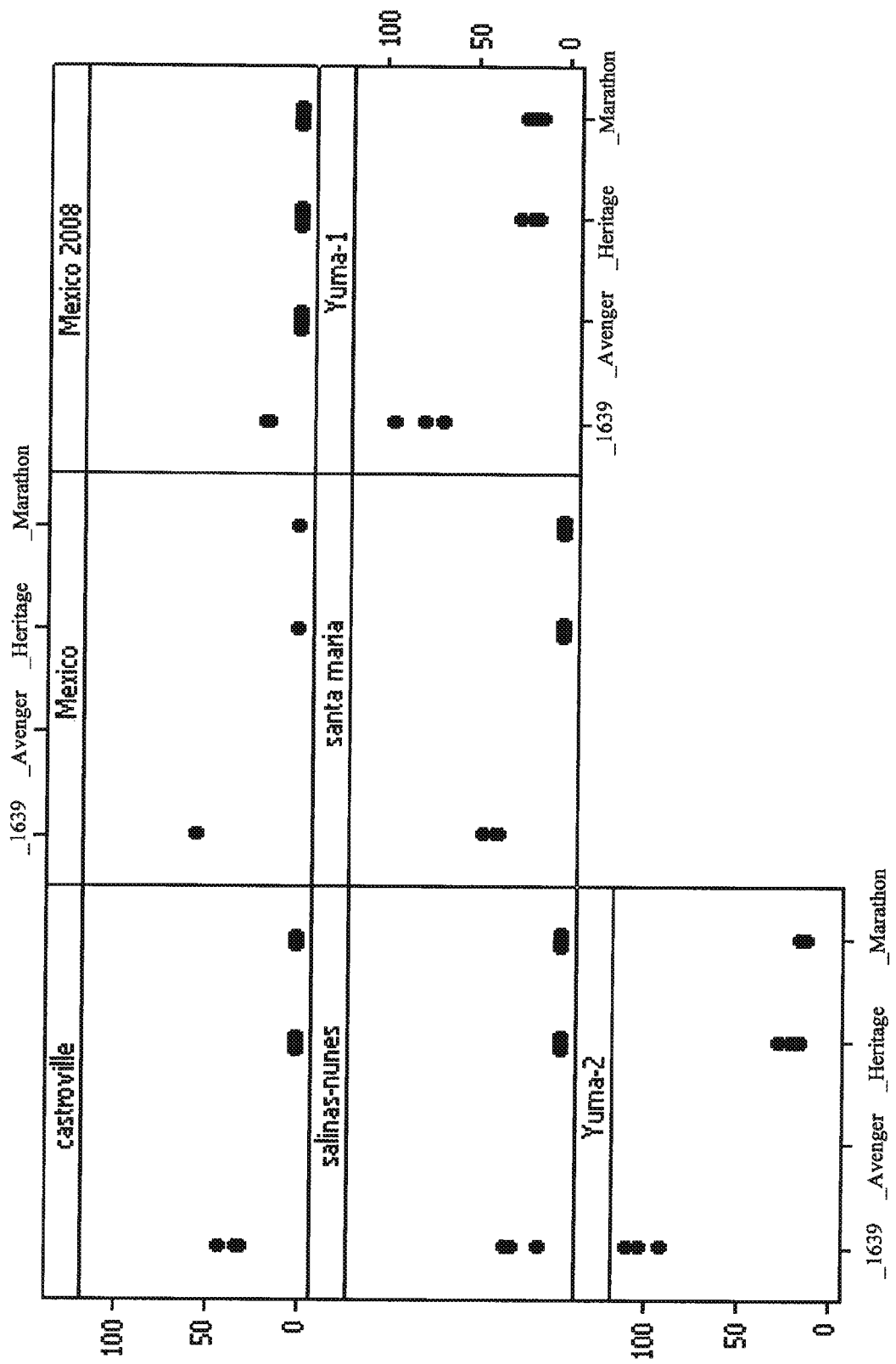
FIG. 5 shows MSP levels in PS05151639 ("1639") and two comparison varieties grown at five different locations in one growing season. Trials were conducted in RCB with 3-4 replicates per variety or in strip plots, unreplicated within a location. MSB was quantified by standard methods.
Figure 6:
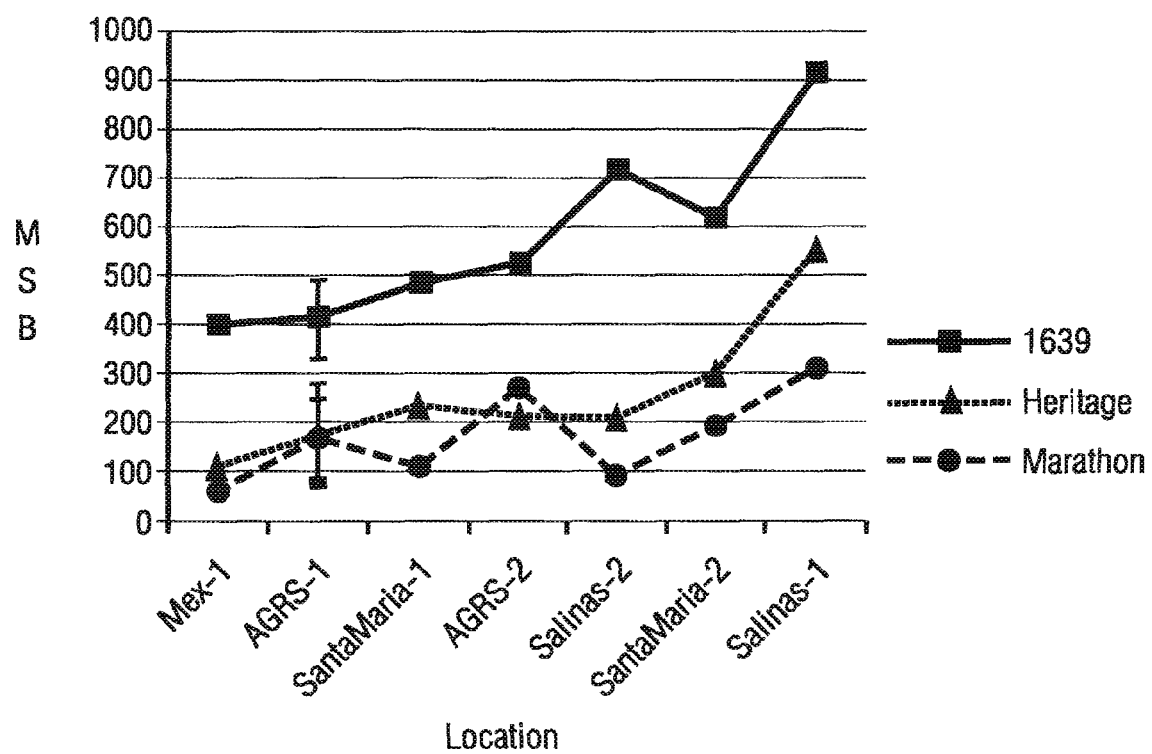
FIG. 6 shows MSB LSM (least-squared means) analysis for each location×planting combination shown in FIG. 2. p-values show that PS05151639 ("1639") has a significantly higher MSB content than the comparison varieties (p<0.15).
Figure 7:
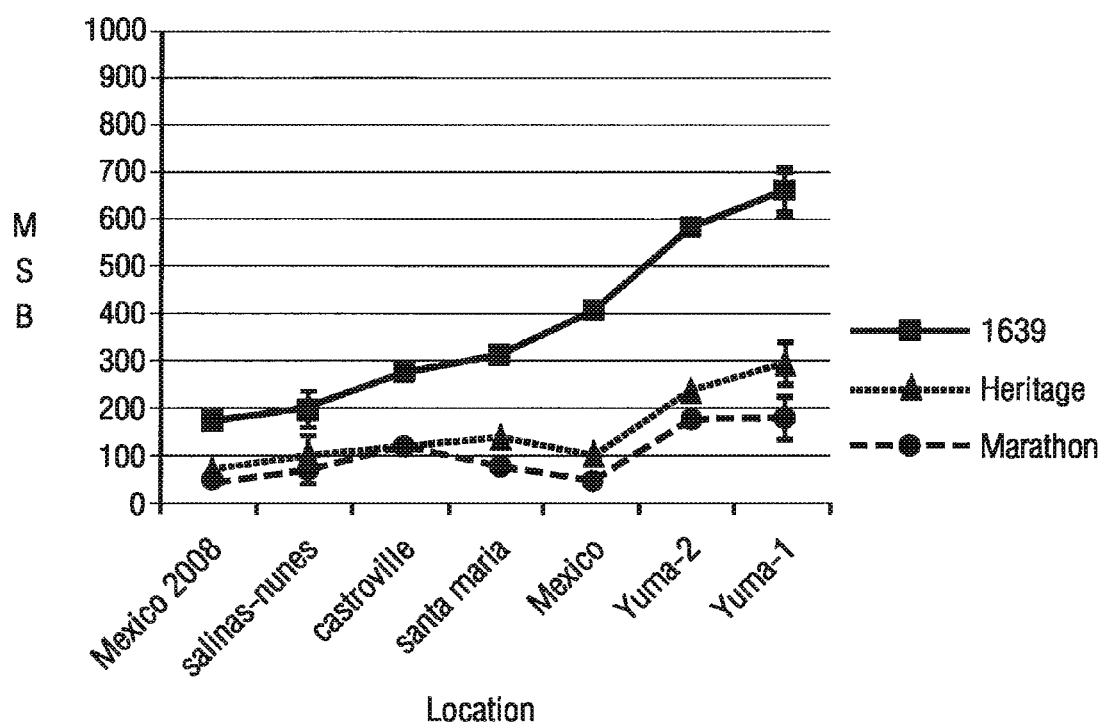
FIG. 7 shows MSB LSM (least-squared means) analysis for each location×planting combination shown in FIG. 3. p-values show that PS05151639 ("1639") has a significantly higher MSB content than the comparison varieties (p<0.10).
Figure 8:
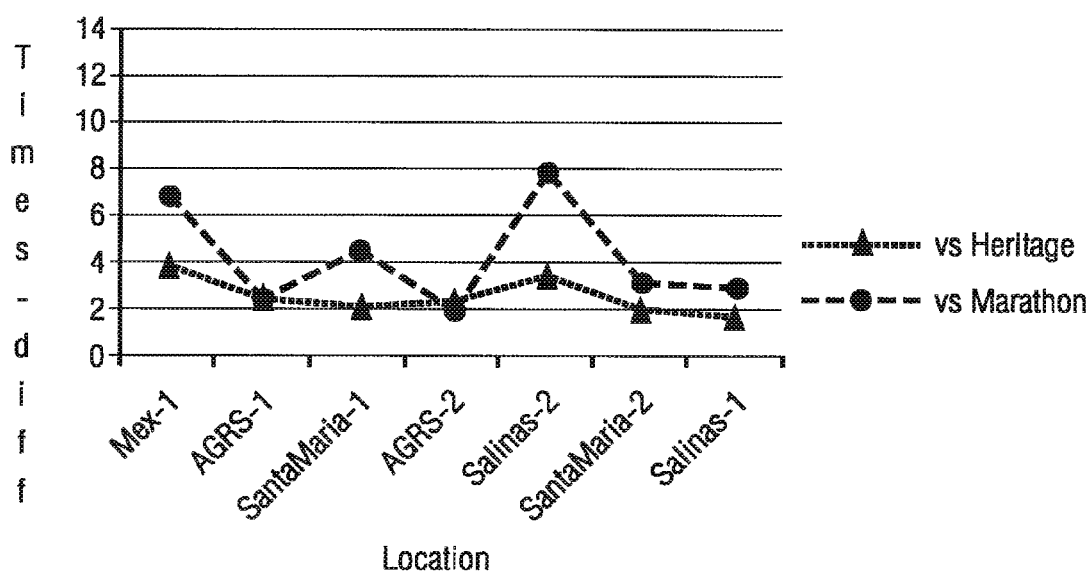
FIG. 8 shows MSB times-difference analysis for each location×planting combination shown in FIG. 2.
Figure 9:
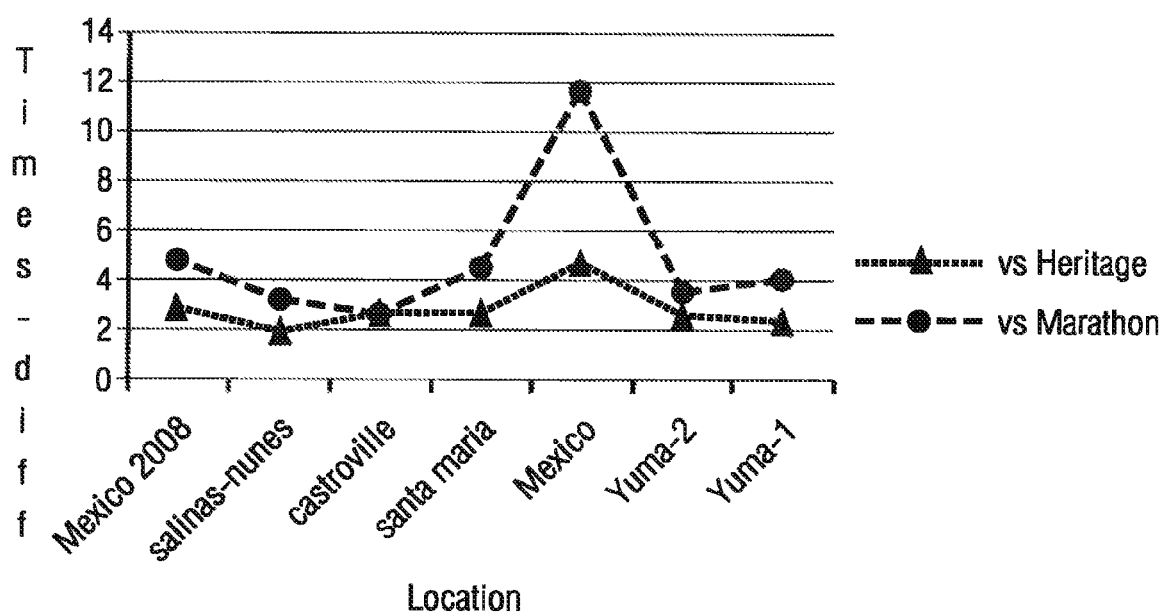
FIG. 9 shows MSB times-difference analysis for each location×planting combination shown in FIG. 3.
Figure 10:
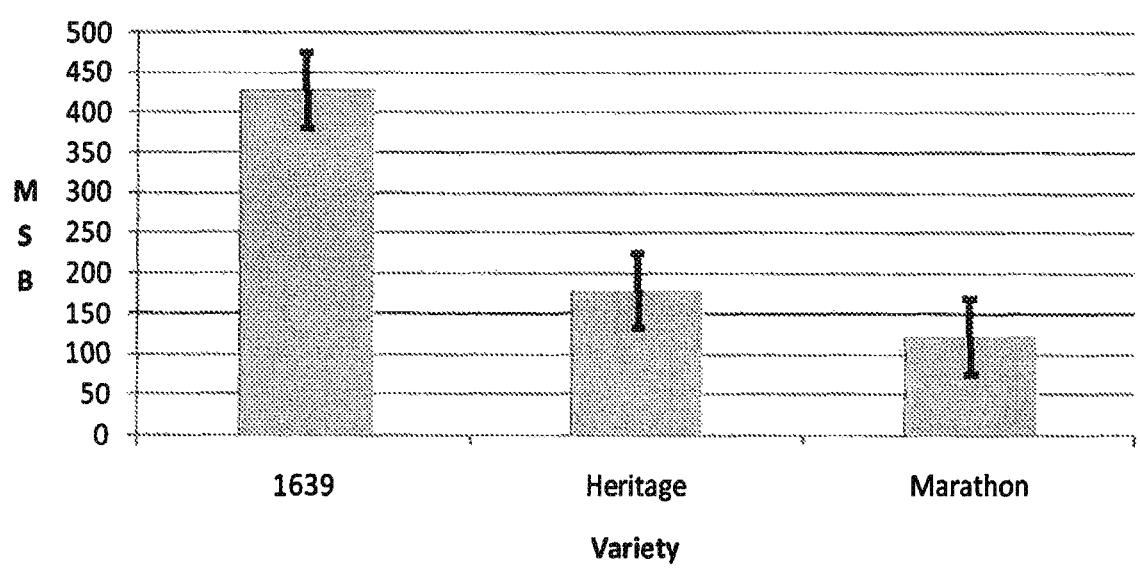
FIG. 10 shows a combined analysis of MSB levels across two replicates and multiple locations (data from FIG. 2 and FIG. 3 combined). Data for PS05151639 is labeled "1639".
Figure 11:
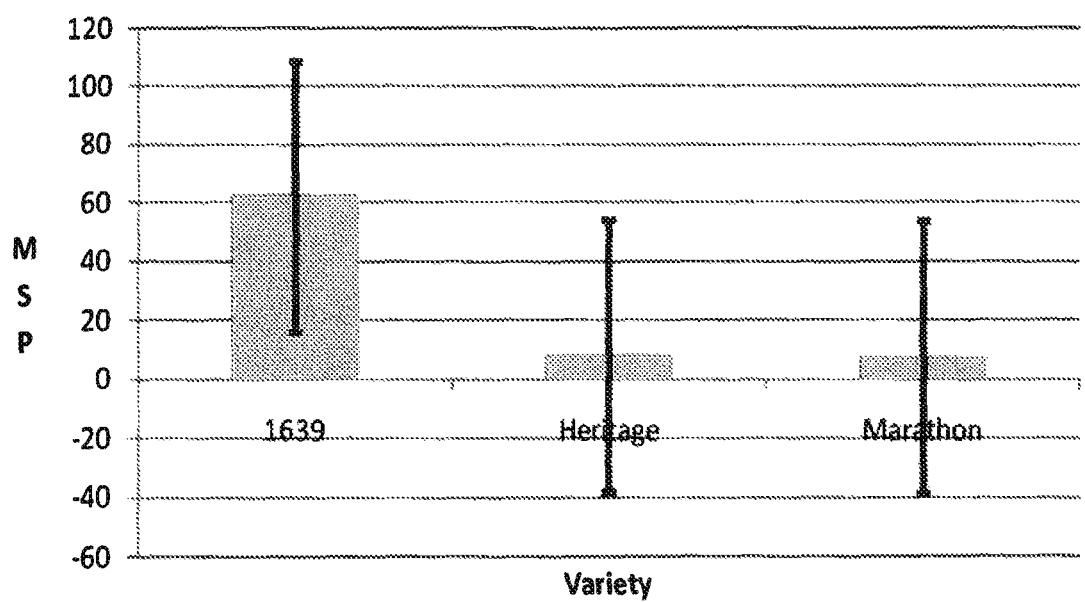
FIG. 11 shows a combined analysis of MSP levels across two replicates and multiple locations (data from FIG. 2 and FIG. 3 combined). Data for PS05151639 is labeled "1639".

The invention provides methods and compositions relating to plants, seeds and derivatives of PS05151639 broccoli hybrid PS05151639 and/or broccoli lines BRM 51-1162 and BRL 51-1128. The parent lines show uniformity and stability within the limits of environmental influence for the traits described hereinafter. By crossing the parent lines, uniform plants of hybrid PS05151639 can be obtained.

In one embodiment, a plant of the invention comprises one or more improved trait selected from increased levels of the phytochemicals MSP (glucoiberin) and/or MSB (glucoraphanin) levels. The development of broccoli hybrid PS05151639 and its parent lines can be summarized as follows.

A. ORIGIN AND BREEDING HISTORY OF BROCCOLI HYBRID PS05151639

The parents of hybrid PS05151639 are BRM 51-1162 and BRL 51-1128. These parents were created as follows.

Line FT-69 is a line developed by the John Innes Center, UK which has elevated levels of the phytochemical MSP (glucoiberin). It was created by crossing a wild relative of domesticated broccoli, *Brassica villosa*, with a domesticated broccoli, *Brassica oleracea*. FT-69 was backcrossed to the adapted broccoli parent line BRM 51-19. After each cross, plants were selected based on phenotype similarities to the recurrent parent BRM 51-19, and analyzed for levels of MSP (glucoiberin) and the additional phytochemical MSB (glucoraphanin). The finished line was named BRM 51-1162.

BRL 51-1128 was developed from an original cross of BRL 51-99 single cross (SC) with a cytoplasmic male sterile (CMS) Broccoli having the cabbage Blue Dynasty cytoplasm. BRL 51-99 was the doubled haploid inbred line 398-1254. A back cross program using BRL 51-99 as the recurrent pollen parent for 5 generations was pursued. After five generations of backcrossing, BRL 51-1128 CMS BC 5 line was sent to a production site and the breeder source 05BajaBK 76-2A/CP 1915 was created and used in foundation seed program for this inbred.

B. PHYSIOLOGICAL AND MORPHOLOGICAL CHARACTERISTICS OF BROCCOLI HYBRID PS05151639, BROCCOLI LINE BRM 51-1162 AND BROCCOLI LINE BRL 51-1128

In accordance with one aspect of the present invention, there is provided a plant having the physiological and morphological characteristics of broccoli hybrid PS05151639 and the parent lines thereof. A description of the physiological and morphological characteristics of such plants is presented in Tables 1-3.

TABLE 1

Physiological and Morphological Characteristics of Hybrid PS05151639

| CHARACTERISTIC | PS05151639 | Heritage |
|---|---|---|
| Species | *Brassica oleracea* var. *italica L.* | *Brassica oleracea* var. *italica L.* |
| Region of Adaptation (area where best adapted in USA) | Pacific Coast | Pacific Coast |
| Maturity | | |
| Fall Planted (days from direct seeding to 50% harvest) | 129.5<br>Rep 1 Jan. 8, 2009 rep 2 Jan. 22, 2009<br>Rep 1 May 21, 2009 rep 2 May 28, 2009 | 129.5<br>Rep 1 Jan. 8, 2009 rep 2 Jan. 22, 2009<br>Rep 1 May 21, 2009 rep 2 May 28, 2009 |
| Fall Planted (days from transplanting to 50% harvest) | 80<br>Rep 1 Feb. 27, 2009 rep 2 Mar. 12, 2009 | 80<br>Rep 1 Feb. 27, 2009 rep 2 Mar. 12, 2009 |
| Fall Planted (length of harvest period in days) | 1<br>Rep 1 May 21, 2009 rep 2 May 28, 2009<br>Rep 1 May 21, 2009 rep 2 May 28, 2009 | 1<br>Rep 1 May 21, 2009 rep 2 May 28, 2009<br>Rep 1 May 21, 2009 rep 2 May 28, 2009 |
| Harvest Season (main crop at 50% harvest) | Spring/Summer | Spring/Summer |
| Time of Harvest Maturity (50% of plants) | Early<br>(Galaxy, Packman, Scorpio) | Medium |
| Time of Beginning of Flowering (50% of plants with at least 10% flowers) | Medium<br>(Coaster, Cruiser) | Medium |
| Seedling | | |
| Cotyledon Color | Medium Green | Medium Green |
| Cotyledon Color (RHS color chart value) | 132D | 132D |
| Cotyledon Anthocyanin | Absent | Weak |
| Hypocotyl Anthocyanin | Intermediate | Intermediate |
| Plant | | |
| Plant Height (at harvest, cm) | 68.2 | 74.9 |
| Head Height (at harvest, cm) | 35.9 | 38.8 |
| Height (at harvest maturity, cm) | Medium<br>(Coaster) | Tall |
| Number of Stems | One<br>(Ramoso Calabrese, Shogun) | One |
| Branches | Many | Medium |
| Habit | Intermediate | Intermediate |
| Market Class | Both | Both |
| Life Cycle | Annual | Annual |
| Type of Variety | First Generation Hybrid | Hybrid |
| Leaf | | |
| Width | Medium<br>(Buccaneer, Green Belt) | Broad |
| Length (including petiole) | Long<br>(Green Duke, Laser) | Long |
| Number of Lobes | Medium<br>(Coaster, Topper) | Many |
| Attitude (at beginning of head formation) | Semi-erect<br>(Arcadia, Asti, Civet, Claudia) | Semi Erect |
| Outer Leaves | | |
| Number of Leaves Per Plant (at harvest) | 16.09 | 14.3 |
| Width (at midpoint of plant including petiole, cm) | 16.4 | 18 |
| Length (at midpoint of plant including petiole, cm) | 54.6 | 60.1 |
| Petiole Length (cm) | 22.5 | 23.8 |
| Length | Long<br>(Groene Calabrese, Premium Crop) | Long |
| Leaf Ratio - Length/Width | 5:1 | 5:1 |
| Leaf Attachment | Petiolate | Petiolate |
| Wax Presence | Intermediate | Intermediate |
| Foliage Color (with wax, if present) | Dark Green | Dark Green |

TABLE 1-continued

Physiological and Morphological Characteristics of Hybrid PS05151639

| CHARACTERISTIC | PS05151639 | Heritage |
|---|---|---|
| Foliage Color (with wax, if present, RHS color chart value) | 139A | 136A |
| Leaf Shape | Narrow Elliptic | Narrow Elliptic |
| Leaf Base | Blunt | Blunt |
| Leaf Apex | Blunt | Blunt |
| Leaf Margins | Very Wavy | Very Wavy |
| Leaf Veins | Thick | Thick |
| Midrib | Raised | Raised |
| Attitude (leaf angle from ground) | Erect (80-100 degrees) | Erect |
| Torsion of Leaf Tip | Intermediate | Intermediate |
| Profile of Upper Side of Leaf | Concave | Planar |
| Leaf Blade | | |
| Color | Green (Claudia, Verflor) | Green |
| Intensity of Color | Dark | Dark |
| Anthocyanin Coloration | Absent (Claudia, Embassy) | Absent |
| Undulation of Margin | Medium (Citation) | Medium |
| Dentation of Margin | Medium (Buccaneer) | Medium |
| Blistering | Medium (Medium Late 145, Skiff) | Medium |
| Head | | |
| Length of Branching at Base (excluding stem) | Very Long (A Getti di Napoli) | Short |
| Diameter (at widest point, at market maturity, cm) | 15.4 | 14.4 |
| Depth (at market maturity, cm) | 14.2 | 10.9 |
| Weight (market trimmed, at market maturity, grams) | 391.4 | 387.5 |
| Color (at market maturity) | Medium Green (Idol, Verflor) | Dark Green |
| Intensity of Color | Medium | Dark |
| Color (at market maturity, RHS color chart value) | 137B | N138B |
| Anthocyanin Coloration | Present (Brigadeer, Shogun, Viola) | Absent |
| Intensity of Anthocyanin Coloration | Weak (Brigadeer) | |
| Shape (at market maturity) | Circular (Esquire) | Transverse Elliptic |
| Dome Shape (at market maturity) | Domed | Semi Domed |
| Size (at market maturity) | Medium (Dundee, Early Man) | Medium |
| Compactness/Firmness (at market maturity) | Short Pedicels/Tight/Firm (Captain) | Short Pedicels/Tight/Firm |
| Surface Knobbling (at market maturity) | Medium (Southern Comet) | Fine |
| Texture | Coarse (Citation) | Fine |
| Bead Size (at market maturity) | Small | Small |
| Flower Buds (at market maturity) | Uneven in Size (Cateye) | Even In Size |
| Anthocyanin Coloration of Leaf Axils (at market maturity) | Absent | Absent |
| Anthocyanin Coloration of Leaf Veins (at market maturity) | Absent | Absent |
| Anthocyanin Coloration of Leaf Blade (at market maturity) | Absent | Absent |
| Anthocyanin Coloration of Entire Plant (at market maturity) | Present | Present |
| Anthocyanin Coloration | Absent | Absent |

TABLE 1-continued

Physiological and Morphological Characteristics of Hybrid PS05151639

| CHARACTERISTIC | PS05151639 | Heritage |
|---|---|---|
| of Leaf Petiole (at market maturity) | (Claudia, Embassy) | |
| Color of Head Leaves (at market maturity) | Green | Green |
| Color of Head Leaves (at market maturity, RHS color chart value) | 137A | 137A |
| Bracts | Absent (Gem, Orion) | Absent |
| Secondary Heads (at market maturity) | Axillary along entire main stem up to main head | Axillary along entire main stem up to main head |
| Prominence of Secondary Heads (at market maturity) | Weak | Weak |
| Number of Secondary Heads (at market maturity) | 1.4 | 1.3 |
| Flower | | |
| Color | Cream | Yellow |
| Intensity of Yellow Color | | Light |
| Color (RHS color chart value) | 157D | 5C |
| Stalk Color | Green | Green |
| Stalk Color (RHS color chart value) | 137A | 137B |
| Male Sterility | Present (Chevalier, Montop) | Present |

*These are typical values. Values may vary due to environment. Other values that are substantially equivalent are also within the scope of the invention.

TABLE 2

Physiological and Morphological Characteristics of Line BRM 51-1162

| CHARACTERISTIC | BRM 51-1162 | Heritage |
|---|---|---|
| Species | *Brassica oleracea* var. *italica* L. | *Brassica oleracea* var. *italica* L. |
| Region of Adaptation (area where best adapted in USA) | Pacific Coast | Pacific Coast |
| Maturity | | |
| Fall Planted (days from direct seeding to 50% harvest) | 136<br>Rep 1 Jan. 8, 2009 rep 2 Jan. 22, 2009<br>Rep 1 May 28, 2009 rep 2 Jun. 3, 2009 | 129.5<br>Rep 1 Jan. 8, 2009 rep 2 Jan. 22, 2009<br>Rep 1 May 21, 2009 rep 2 May 28, 2009 |
| Fall Planted (days from transplanting to 50% harvest) | 86.5<br>Rep 1 Feb. 27, 2009 rep 2 Mar. 12, 2009 | 80<br>Rep 1 Feb. 27, 2009 rep 2 Mar. 12, 2009 |
| Fall Planted (length of harvest period in days) | 1<br>Rep 1 May 28, 2009 rep 2 Jun. 3, 2009<br>Rep 1 May 28, 2009 rep 2 Jun. 3, 2009 | 1<br>Rep 1 May 21, 2009 rep 2 May 28, 2009<br>Rep 1 May 21, 2009 rep 2 May 28, 2009 |
| Harvest Season (main crop at 50% harvest) | Spring/Summer | Spring/Summer |
| Time of Harvest Maturity (50% of plants) | Very Late (Late Purple Sprouting) | Medium |
| Time of Beginning of Flowering (50% of plants with at least 10% flowers) | Medium-Late | Medium |
| Seedling | | |
| Cotyledon Color | Medium Green | Medium Green |
| Cotyledon Color (RHS color chart value) | 132D | 132D |
| Cotyledon Anthocyanin | Weak | Weak |
| Hypocotyl Anthocyanin | Weak | Intermediate |
| Plant | | |
| Plant Height (at harvest, cm) | 52 | 74.9 |
| Head Height (at harvest, cm) | 20.25 | 38.8 |
| Height (at harvest maturity) | Short (Packman, Primor) | Tall |

TABLE 2-continued

Physiological and Morphological Characteristics of Line BRM 51-1162

| CHARACTERISTIC | BRM 51-1162 | Heritage |
|---|---|---|
| Number of Stems | One<br>(Ramoso Calabrese, Shogun) | One |
| Branches | Many | Medium |
| Habit | Compact | Intermediate |
| Market Class | Both | Both |
| Life Cycle | Annual | Annual |
| Type of Variety | Inbred | Hybrid |
| Leaf | | |
| Width | Narrow<br>(Arcadia, Brigadeer) | Broad |
| Length (including petiole) | Long<br>(Green Duke, Laser) | Long |
| Number of Lobes | Few<br>(Early White Sprouting) | Many |
| Attitude (at beginning of head formation) | Semi-erect<br>(Arcadia, Asti, Civet, Claudia) | Semi Erect |
| Outer Leaves | | |
| Number of Leaves Per Plant (at harvest) | 14.09 | 14.3 |
| Width (at midpoint of plant including petiole, cm) | 18.3 | 18 |
| Length (at midpoint of plant including petiole, cm) | 47.8 | 60.1 |
| Petiole Length (cm) | 18.1 | 23.8 |
| Leaf Ratio - Length/Width | 4:1 | 5:1 |
| Leaf Attachment | Petiolate | Petiolate |
| Wax Presence | Intermediate | Intermediate |
| Foliage Color (with wax, if present) | Dark Green | Dark Green |
| Foliage Color (with wax, if present, RHS color chart value) | 138A | 136A |
| Leaf Shape | Narrow Elliptic | Narrow Elliptic |
| Leaf Base | Blunt | Blunt |
| Leaf Apex | Blunt | Blunt |
| Leaf Margins | Very Wavy | Very Wavy |
| Leaf Veins | Thick | Thick |
| Midrib | Raised | Raised |
| Attitude (leaf angle from ground) | Erect<br>(80-100 degrees) | Erect |
| Torsion of Leaf Tip | Intermediate | Intermediate |
| Profile of Upper Side of Leaf | Planar | Planar |
| Petiole | | |
| Length | Long<br>(Groene Calabrese, Premium Crop) | Long |
| Leaf Blade | | |
| Color | Green<br>(Claudia, Verflor) | Green |
| Intensity of Color | Dark | Dark |
| Anthocyanin Coloration | Present<br>(Buccaneer, Pascal) | Absent |
| Undulation of Margin | Medium<br>(Citation) | Medium |
| Dentation of Margin | Medium<br>(Buccaneer) | Medium |
| Blistering | Medium<br>(Medium Late 145, Skiff) | Medium |
| Head | | |
| Length of Branching at Base (excluding stem) | Short<br>(Brigadeer, Buccaneer, Emperor) | Short |
| Diameter (at widest point, at market maturity, cm) | 13 | 14.4 |
| Depth (at market maturity, cm) | 13.2 | 10.9 |

TABLE 2-continued

Physiological and Morphological Characteristics of Line BRM 51-1162

| CHARACTERISTIC | BRM 51-1162 | Heritage |
|---|---|---|
| Weight (market trimmed, at market maturity, grams) | 355.6 | 387.5 |
| Color (at market maturity) | Blue-green (Buccaneer) | Dark Green |
| Intensity of Color | Medium | Dark |
| Color (at market maturity, RHS color chart value) | 137B | N138B |
| Anthocyanin Coloration | Absent (Early White Sprouting) | Absent |
| Shape (at market maturity) | Circular (Esquire) | Transverse Elliptic |
| Dome Shape (at market maturity) | Semi-domed | Semi Domed |
| Size (at market maturity) | Small (Orbit, Scorpio) | Medium |
| Compactness/Firmness (at market maturity) | Short Pedicels/Tight/Firm (Captain) | Short Pedicels/Tight/Firm |
| Surface Knobbling (at market maturity) | Medium (Southern Comet) | Fine |
| Texture | Fine (Auriga, Bishop, Green Top) | Fine |
| Bead Size (at market maturity) | Small | Small |
| Flower Buds (at market maturity) | Uneven in Size (Cateye) | Even In Size |
| Anthocyanin Coloration of Leaf Axils (at market maturity) | Absent | Absent |
| Anthocyanin Coloration of Leaf Veins (at market maturity) | Absent | Absent |
| Anthocyanin Coloration of Leaf Blade (at market maturity) | Absent | Absent |
| Anthocyanin Coloration of Entire Plant (at market maturity) | Present | Present |
| Anthocyanin Coloration of Leaf Petiole (at market maturity) | Absent (Claudia, Embassy) | Absent |
| Color of Head Leaves (at market maturity) | Green | Green |
| Color of Head Leaves (at market maturity, RHS color chart value) | 137A | 137A |
| Bracts | Present (Ramoso Calabrese) | Absent |
| Secondary Heads (at market maturity) | Completely Absent (Scorpio, Zeus) | Axillary along entire main stem up to main head |
| Prominence of Secondary Heads (at market maturity) | | Weak |
| Number of Secondary Heads (at market maturity) | 0 | 1.3 |
| Flower | | |
| Color | Cream | Yellow |
| Intensity of Yellow Color | | Light |
| Color (RHS color chart value) | 155A | 5C |
| Stalk Color | Green | Green |
| Stalk Color (RHS color chart value) | 138A | 137B |
| Male Sterility | Absent (Marathon) | Present |

*These are typical values. Values may vary due to environment. Other values that are substantially equivalent are also within the scope of the invention.

TABLE 3

Physiological and Morphological Characteristics of Line BRL 51-1128

| CHARACTERISTIC | BRL 51-1128 | Heritage |
|---|---|---|
| Species | *Brassica oleracea* var. *italica L.* | *Brassica oleracea* var. *italica L.* |
| Region of Adaptation (area where best adapted in USA) | Pacific Coast | Pacific Coast |
| Maturity | | |
| Fall Planted (days from direct seeding to 50% harvest) | 129.5<br>Rep 1 Jan. 8, 2009 rep 2 Jan. 22, 2009<br>Rep 1 May 21, 2009 rep 2 May 28, 2009 | 129.5<br>Rep 1 Jan. 8, 2009 rep 2 Jan. 22, 2009<br>Rep 1 May 21, 2009 rep 2 May 28, 2009 |
| Fall Planted (days from transplanting to 50% harvest) | 80<br>Rep 1 Feb. 27, 2009 rep 2 Mar. 12, 2009 | 80<br>Rep 1 Feb. 27, 2009 rep 2 Mar. 12, 2009 |
| Fall Planted (length of harvest period in days) | 1<br>Rep 1 May 21, 2009 rep 2 May 28, 2009<br>Rep 1 May 21, 2009 rep 2 May 28, 2009 | 1<br>Rep 1 May 21, 2009 rep 2 May 28, 2009<br>Rep 1 May 21, 2009 rep 2 May 28, 2009 |
| Harvest Season (main crop at 50% harvest) | Spring/Summer | Spring/Summer |
| Time of Harvest Maturity (50% of plants) | Early<br>(Galaxy, Packman, Scorpio) | Medium |
| Time of Beginning of Flowering (50% of plants with at least 10% flowers) | Late<br>(Shogun, Viola) | Medium |
| Seedling | | |
| Cotyledon Color | Medium Green | Medium Green |
| Cotyledon Color (RHS color chart value) | 132D | 132D |
| Cotyledon Anthocyanin | Weak | Weak |
| Hypocotyl Anthocyanin | Strong | Intermediate |
| Plant | | |
| Plant Height (at harvest, cm) | 52.6 | 74.9 |
| Head Height (at harvest, cm) | 38.2 | 38.8 |
| Height (at harvest maturity) | Short<br>(Packman, Primor) | Tall |
| Number of Stems | More Than One<br>(A Getti di Napoli) | One |
| Branches | Many | Medium |
| Habit | Compact | Intermediate |
| Market Class | Both | Both |
| Life Cycle | Annual | Annual |
| Type of Variety | Inbred | Hybrid |
| Leaf | | |
| Width | Broad<br>(Claudia, Esquire, New Prince) | Broad |
| Length (including petiole) | Long<br>(Green Duke, Laser) | Long |
| Number of Lobes | Few<br>(Early White Sprouting) | Many |
| Attitude (at beginning of head formation) | Semi-erect<br>(Arcadia, Asti, Civet, Claudia) | Semi Erect |
| Outer Leaves | | |
| Number of Leaves Per Plant (at harvest) | 27.7 | 14.3 |
| Width (at midpoint of plant including petiole, cm) | 11.7 | 18 |
| Length (at midpoint of plant including petiole, cm) | 41 | 60.1 |
| Petiole Length (cm) | 16.7 | 23.8 |
| Leaf Ratio - Length/Width | 4:1 | 5:1 |
| Leaf Attachment | Petiolate | Petiolate |
| Wax Presence | Intermediate | Intermediate |
| Foliage Color (with wax, if present) | Purple-green | Dark Green |
| Foliage Color (with wax, if present, RHS color chart value) | 137A | 136A |
| Leaf Shape | Broad Elliptic | Narrow Elliptic |

TABLE 3-continued

Physiological and Morphological Characteristics of Line BRL 51-1128

| CHARACTERISTIC | BRL 51-1128 | Heritage |
|---|---|---|
| Leaf Base | Blunt | Blunt |
| Leaf Apex | Blunt | Blunt |
| Leaf Margins | Slightly Wavy | Very Wavy |
| Leaf Veins | Thick | Thick |
| Midrib | Raised | Raised |
| Attitude (leaf angle from ground) | Erect (80-100 degrees) | Erect |
| Torsion of Leaf Tip | Intermediate | Intermediate |
| Profile of Upper Side of Leaf | Concave | Planar |
| Petiole | | |
| Length | Long (Groene Calabrese, Premium Crop) | Long |
| Leaf Blade | | |
| Color | Green (Claudia, Verflor) | Green |
| Intensity of Color | Dark | Dark |
| Anthocyanin Coloration | Present (Buccaneer, Pascal) | Absent |
| Undulation of Margin | Medium (Citation) | Medium |
| Dentation of Margin | Medium (Buccaneer) | Medium |
| Blistering | Medium (Medium Late 145, Skiff) | Medium |
| Head | | |
| Length of Branching at Base (excluding stem) | Very Long (A Getti di Napoli) | Short |
| Diameter (at widest point, at market maturity, cm) | 12.1 | 14.4 |
| Depth (at market maturity, cm) | 15.75 | 10.9 |
| Weight (market trimmed, at market maturity, grams) | 221.8 | 387.5 |
| Color (at market maturity) | Purple/Violet (Viola) | Dark Green |
| Intensity of Color | Medium | Dark |
| Color (at market maturity, RHS color chart value) | 189A | N138B |
| Anthocyanin Coloration | Present (Brigadeer, Shogun, Viola) | Absent |
| Intensity of Anthocyanin Coloration | Strong | |
| Shape (at market maturity) | Transverse Elliptic Narrow (Citation, Scorpio, Zeus) | Transverse Elliptic |
| Dome Shape (at market maturity) | Domed | Semi Domed |
| Size (at market maturity) | Small (Orbit, Scorpio) | Medium |
| Compactness/Firmness (at market maturity) | Short Pedicels/Tight/Firm (Captain) | Short Pedicels/Tight/Firm |
| Surface Knobbling (at market maturity) | Coarse (Perseus, Regilio) | Fine |
| Texture | Coarse (Citation) | Fine |
| Bead Size (at market maturity) | Small | Small |
| Flower Buds (at market maturity) | Uneven in Size (Cateye) | Even In Size |
| Anthocyanin Coloration of Leaf Axils (at market maturity) | Present | Absent |
| Anthocyanin Coloration of Leaf Veins (at market maturity) | Absent | Absent |
| Anthocyanin Coloration of Leaf Blade (at market maturity) | Present | Absent |
| Anthocyanin Coloration of Entire Plant (at market maturity) | Present | Present |

TABLE 3-continued

Physiological and Morphological Characteristics of Line BRL 51-1128

| CHARACTERISTIC | BRL 51-1128 | Heritage |
|---|---|---|
| Anthocyanin Coloration of Leaf Petiole (at market maturity) | Absent (Claudia, Embassy) | Absent |
| Color of Head Leaves (at market maturity) | Green | Green |
| Color of Head Leaves (at market maturity, RHS color chart value) | 139A | 137A |
| Bracts | Present (Ramoso Calabrese) | Absent |
| Secondary Heads (at market maturity) | Basal | Axillary along entire main stem up to main head |
| Prominence of Secondary Heads (at market maturity) | Strong (Marathon, Tribute) | Weak |
| Number of Secondary Heads (at market maturity) | 1.5 | 1.3 |
| Flower | | |
| Color | Yellow (Brigadeer, Orion) | Yellow |
| Intensity of Yellow Color | Medium (Capitol, Corvet) | Light |
| Color (RHS color chart value) | 3D | 5C |
| Stalk Color | Green | Green |
| Stalk Color (RHS color chart value) | 137B | 137B |
| Male Sterility | Present (Chevalier, Montop) | Present |

*These are typical values. Values may vary due to environment. Other values that are substantially equivalent are also within the scope of the invention.

C. BREEDING BROCCOLI PLANTS

One aspect of the current invention concerns methods for producing seed of broccoli hybrid PS05151639 involving crossing broccoli lines BRM 51-1162 and BRL 51-1128. Alternatively, in other embodiments of the invention, hybrid PS05151639, line BRM 51-1162, or line BRL 51-1128 may be crossed with itself or with any second plant. Such methods can be used for propagation of hybrid PS05151639 and/or the broccoli lines BRM 51-1162 and BRL 51-1128, or can be used to produce plants that are derived from hybrid PS05151639 and/or the broccoli lines BRM 51-1162 and BRL 51-1128. Plants derived from hybrid PS05151639 and/or the broccoli lines BRM 51-1162 and BRL 51-1128 may be used, in certain embodiments, for the development of new broccoli varieties.

The development of new varieties using one or more starting varieties is well known in the art. In accordance with the invention, novel varieties may be created by crossing hybrid PS05151639 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plant of the present invention are particularly well suited for the development of new lines based on the elite nature of the genetic background of the plants. In selecting a second plant to cross with PS05151639 and/or broccoli lines BRM 51-1162 and BRL 51-1128 for the purpose of developing novel broccoli lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high yield, disease tolerance or resistance, and adaptability for soil and climate conditions. Consumer-driven traits, such as a head shape, nutritional value, and taste are other traits that may be incorporated into new lines of broccoli plants developed by this invention.

D. PERFORMANCE CHARACTERISTICS

As described above, hybrid PS05151639 exhibits desirable agronomic traits. The performance characteristics of PS05151639 were the subject of an objective analysis of the performance traits relative to other varieties. The results of the analysis are presented below.

MSB levels were quantitated using standard methods. The data was analyzed using a combined analysis across locations and plantings, considering variety as a fixed effect, and location, planting, reps within (location×planting), location×planting, and their interactions with variety as random effects. Results for MSB are presented in Table 5. Hybrid PS05151639's LS-mean was 428, vs comparison varieties Heritage LSM of 180 and Marathon's of 123. PS05151639 contained 2.4× more MSB than Heritage and 3.5× more than Marathon.

TABLE 4

Performance Characteristics For PS05151639 and Selected Varieties*

| Variety | Plant Traits | | | | | Stem Traits | | |
|---|---|---|---|---|---|---|---|---|
| (average over eight trials) | Size (1 = tall, 9 = short) | Type (1 = erect, 9 = open) | Uniformity (1 = excellent, 9 = poor) | Vigor (1 = very strong, 9 = very weak) | Side Shoots (1 = absent, 9 = very weak) | Size (1 = thick, 9 = thin) | Smoothness 1 = very smooth, 9 = very irregular) | Cleaning ability (1 = very easy, 9 = difficult) |
| PS05151639 Average | 3.6 | 2.3 | 3.79 | 3.3 | 1.5 | 5.8 | 1.92 | 1.5 |
| Marathon Average | 4.8 | 3.5 | 3 | 3.3 | 2.125 | 6 | 1.75 | 1.56 |
| Heritage Average | 3.5 | 2.3 | 3 | 3.3 | 2.25 | 4.6 | 4.42 | 4.06 |

| Variety | Stem Traits | Floret Traits | | | Head Traits | | |
|---|---|---|---|---|---|---|---|
| (average over eight trials) | Lateral Heads (1 = absent. 9 = alot) | Size (1 = tall, 9 = short) | Contrast Color (1 = absent, 9 = >26%) | Pedicel Size (1 = short, 9 = large) | Type (1 = crown, 9 = spear) | Size (cm) (1 = extra large [>7"], 7 = small [<5"]) | Color (1 = dark green, 9 = purple green) |
| PS05151639 Average | 1 | 4 | 5 | 1 | 1 | 5 | 3.59 |
| Marathon Average | 1 | 4 | 5 | 1 | 1 | 5 | 4.34 |
| Heritage average | 1 | 6 | 5 | 1 | 1 | 5 | 1.58 |

| Variety | Head Traits | | | | | | |
|---|---|---|---|---|---|---|---|
| | | | | | Weight | Defects | |
| (average over eight trials) | Shape (1 = high dome, 9 = flat) | Bead Size (1 = very fine, 9 = variable) | Firmness (1 = very firm, 9 = soft) | Smoothness (1 = very smooth, 9 = very irregular) | (1 = very heavy [<400 gr], 9 = light [<200 gr]) | Hollow Stem (1 = 100% steam solid, 9 = 76-100% hollow) | Stem Oxidatin (1 = absent, 9 = severe) |
| PS05151639 Average | 2.4 | 4 | 5.2 | 5.2 | 5.25 | 1 | 1 |
| Marathon Average | 3.9 | 4.05 | 5.1 | 4.3 | 6.75 | 1 | 1 |
| Heritage average | 3.1 | 4.125 | 3.3 | 3.3 | 5 | 1.125 | 1 |

| Variety | Defects | | | | | Harvest | |
|---|---|---|---|---|---|---|---|
| (average over eight trials) | Bracting (1 = absent, 9 = severe) | Cat eye ( 1 = absent, 9 = severe) | Brown Bead (1 = absent, 9 = severe) | Open bead (1 = absent, 9 = present) | Diseases (1 = absent, 9 = severe) | Holding Ability (field) (1 = good, 9 = bad) | Overall (1 = advance, 9 = drop) |
| PS05151639 Average | 1 | 2.5 | 1.06 | 1 | 1 | 1.625 | 4.8 |
| Marathon Average | 1 | 2.6 | 1 | 1 | 1 | 1.625 | 4.9 |
| Heritage Average | 1 | 2.5 | 1 | 1 | 1 | 1 | 3.5 |

*Based on scales as indicated

TABLE 5

MSB Levels For PS05151639 and Selected Varieties

| Variety | MSB LSM | Std. Error | Difference | X-Difference |
|---|---|---|---|---|
| PS05151639 | 428 | 46.2 | | |
| Heritage | 180 | 46.2 | 249 | 2.4X |
| Marathon | 123 | 46.2 | 305 | 3.5X |

MSP levels were quantitated using standard methods. The data was analyzed using a combined analysis across locations and plantings, considering variety as fixed effect, and location, planting, reps within (location×planting), location× planting, and their interactions with variety as random effects. Results for MSP are presented in Table 6. Hybrid PS05151639's LS-mean was 62, vs comparison varieties Heritage LSM of 8 and Marathon's LSM of 7. PS05151639's MSB was 7.8× that of Heritage and 8.5× that of Marathon.

TABLE 6

Performance Characteristics For PS05151639 and Selected Varieties

| Variety | MSP LSM | Std. Error | Difference | X-Difference |
|---|---|---|---|---|
| PS05151639 | 62 | 8.2 | | |
| Heritage | 8 | 8.2 | 54 | 7.8X |
| Marathon | 7 | 8.2 | 55 | 8.5X |

MSB and MSP levels were quantitated in the lines BRL 51-1128 and BRM 51-1162 using standard methods. Results of this analysis are presented in Table 7.

TABLE 7

Performance Characteristics For BRL 51-1128 and BRM 51-1162

| Variety | Glucoraphanin (MSB) micromoles/gram fresh weight | Glucoiberin (MSP) micromoles/gram fresh weight |
|---|---|---|
| BRL 51-1128 CMS | 1.026 | 0.000* |
| BRL 51-1128 CMS | 1.256 | 0.000* |
| BRL 51-1128 CMS | 1.420 | 0.168 |
| BRM 51-1162 | 0.785 | 0.798 |
| BRM 51-1162 SC | 1.092 | 0.972 |
| BRM 51-1162 SC | 1.237 | 1.089 |
| BRM 51-1162 SC | 1.598 | 1.402 |
| BRM 51-1162 SC | 1.552 | 1.531 |
| BRM 51-1162 SC | 1.933 | 1.609 |
| BRM 51-1162 SC | 1.230 | 1.431 |
| BRM 51-1162 SC | 1.480 | 1.761 |
| BRM 51-1162 SC | 1.440 | 1.912 |
| BRM 51-1162 SC | 1.606 | 1.806 |
| BRM 51-1162 SC | 1.873 | 2.444 |
| BRM 51-1162 SC | 2.237 | 2.443 |
| BRM 51-1162 SC | 2.145 | 2.032 |

*no measurable glucoiberin (MSP)

E. FURTHER EMBODIMENTS OF THE INVENTION

In certain aspects of the invention, plants described herein are provided modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those broccoli plants which are developed by a plant breeding technique called backcrossing, wherein essentially all of the desired morphological and physiological characteristics of a variety are recovered in addition to the single locus transferred into the variety via the backcrossing technique. By essentially all of the desired morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental broccoli plant which contributes the locus for the desired characteristic is termed the nonrecurrent or donor parent. This terminology refers to the fact that the nonrecurrent parent is used one time in the backcross protocol and therefore does not recur. The parental broccoli plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a broccoli plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the back-cross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny broccoli plants of a backcross in which PS05151639 is the recurrent parent comprise (i) the desired trait from the non-recurrent parent and (ii) all of the physiological and morphological characteristics of broccoli hybrid PS05151639 as determined at the 5% significance level when grown in the same environmental conditions.

Broccoli varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of broccoli plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. PLANTS DERIVED BY GENETIC ENGINEERING

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for broccoli plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to the broccoli plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a broccoli plant according to the invention. Non-limiting examples of particular genes and corresponding phenotypes one may choose to introduce into a broccoli plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. DEFINITIONS

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a broccoli variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a broccoli plant by transformation.

H. DEPOSIT INFORMATION

A deposit of broccoli hybrid PS05151639 and lines BRM 51-1162 and BRL 51-1128, disclosed above and recited in the claims, has been made with the American Type Culture Collection (ATCC), 10801 University Blvd., Manassas, Va. 20110-2209. The date of the deposits made was Dec. 23, 2008. The accession numbers for those deposited seeds of broccoli hybrid PS05151639 and inbred parent lines BRM 51-1162 and BRL 51-1128 are ATCC Accession Number PTA-9676, ATCC Accession Number PTA-9675, and ATCC Accession Number PTA-9674, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Klee et al., *Bio-Technology*, 3(7):637-642, 1985.
Kuhlemeier et al., *Plant Cell*, 1:471, 1989.
Marcotte et al., *Nature*, 335:454, 1988.
Marcotte et al., *Plant Cell*, 1:969, 1989.
Odel et al., *Nature*, 313:810, 1985.
Omirulleh et al., *Plant Mol. Biol.*, 21(3):415-428, 1993.
Potrykus et al., *Mol. Gen. Genet.*, 199:183-188, 1985.
Roshal et al., *EMBO J.*, 6:1155, 1987.
Schaffner and Sheen, *Plant Cell*, 3:997, 1991.
Schernthaner et al., *EMBO J.*, 7:1249, 1988.
Siebertz et al., *Plant Cell*, 1:961, 1989.
Simpson et al., *EMBO J.*, 4:2723, 1985.
Terada and Shimamoto, *Mol. Gen. Genet.*, 220:389, 1990.
Uchimiya et al., *Mol. Gen. Genet.*, 204:204, 1986.
Wang et al., *Science*, 280:1077-1082, 1998.
Williams et al., *Nucleic Acids Res.*, 1 8:6531-6535, 1990.
WO 99/31248

What is claimed is:

1. A broccoli plant comprising at least a first set of the chromosomes of broccoli line BRM 51-1162 or broccoli line BRL 51-1128, a sample of seed of said lines having been deposited under ATCC Accession Number PTA-9675, and ATCC Accession Number PTA-9674, respectively.

2. A seed comprising at least a first set of the chromosomes of broccoli line BRM 51-1162 or broccoli line BRL 51-1128, a sample of seed of said lines having been deposited under ATCC Accession Number PTA-9675, and ATCC Accession Number PTA-9674, respectively.

3. The plant of claim 1, which is inbred.

4. The plant of claim 1, which is hybrid.

5. The plant of claim 4, wherein the hybrid plant is broccoli hybrid PS05151639, a sample of seed of said hybrid PS05151639 having been deposited under ATCC Accession Number PTA-9676.

6. The plant of claim 3, wherein the inbred plant is line BRM 51-1162 or line BRL 51-1128.

7. A plant part of the plant of claim 1.

8. The plant part of claim 7, further defined as a leaf, a ovule, a floret, pollen, a head, or a cell.

9. A broccoli plant, or a part thereof, having all the physiological and morphological characteristics of the broccoli plant of claim 5.

10. A broccoli plant, or a part thereof, having all the physiological and morphological characteristics of the broccoli plant of claim 6.

11. A tissue culture of regenerable cells of the plant of claim 1.

12. The tissue culture according to claim 11, comprising cells or protoplasts from a plant part selected from the group consisting of embryos, meristems, cotyledons, pollen, leaves, anthers, roots, root tips, pistil, flower, seed and stalks.

13. A broccoli plant regenerated from the tissue culture of claim 12, wherein said plant has all the physiological and morphological characteristics of the broccoli plant comprising at least a first set of the chromosomes of broccoli line BRM 51-1162 or broccoli line BRL 51-1128, a sample of seed of said lines having been deposited under ATCC Accession Number PTA-9675, and ATCC Accession Number PTA-9674, respectively.

14. A method of vegetatively propagating the plant of claim 1 comprising the steps of:
(a) collecting tissue capable of being propagated from a plant according to claim 1;
(b) cultivating said tissue to obtain proliferated shoots; and
(c) rooting said proliferated shoots to obtain rooted plantlets.

15. The method of claim 14, further comprising growing plants from said rooted plantlets.

16. A method of introducing a desired trait into a broccoli line comprising:
(a) crossing a plant of line BRM 51-1162 or BRL 51-1128, a sample of seed of said lines having been deposited under ATCC Accession Number PTA-9675, and ATCC Accession Number PTA-9674, respectively, with a second broccoli plant that comprises a locus conferring a desired trait to produce F1 progeny;
(b) selecting an F1 progeny that comprises the locus and desired trait;
(c) crossing the selected F1 progeny with a plant of line BRM 51-1162 or BRL 51-1128 to produce backcross progeny;
(d) selecting backcross progeny comprising the desired trait and the physiological and morphological characteristic of broccoli line BRM 51-1162 or BRL 51-1128; and
(e) repeating steps (c) and (d) three or more times to produce selected fourth or higher backcross progeny that comprise the locus and desired trait.

17. A broccoli plant produced by the method of claim 16, wherein said plant comprises the desired trait and otherwise comprises essentially all of the morphological and physiological characteristics of the recurrent parent broccoli line BRM 51-1162 or BRL 51-1128.

18. A method of producing a plant comprising an added desired trait, the method comprising introducing a transgene conferring the desired trait into a plant of hybrid PS05151639, line BRM 51-1162 or line BRL 51-1128, a sample of seed of said hybrid and lines having been deposited under ATCC Accession Number PTA-9676, ATCC Accession Number PTA-9675, and ATCC Accession Number PTA-9674, respectively.

19. A method for producing a seed of a plant derived from at least one of hybrid PS05151639, line BRM 51-1162 or line BRL 51-1128 comprising the steps of:
(a) crossing a broccoli plant of hybrid PS05151639, line BRM 51-1162 or line BRL 51-1128 with a second broccoli plant; a sample of seed of said hybrid and lines having been deposited under ATCC Accession Number PTA-9676, ATCC Accession Number PTA-9675, and ATCC Accession Number PTA-9674, respectively; and
(b) allowing seed of a hybrid PS05151639, line BRM 51-1162 or line BRL 51-1128-derived broccoli plant to form.

20. The method of claim 19, further comprising the steps of:
(c) crossing a plant grown from said hybrid PS05151639, BRM 51-1162 or BRL 51-1128-derived broccoli seed with itself or a second broccoli plant to yield additional hybrid PS05151639, BRM 51-1162 or BRL 51-1128-derived broccoli seed;
(d) growing said additional hybrid PS05151639, BRM 51-1162 or BRL 51-1128-derived broccoli seed of step (c) to yield additional hybrid PS05151639, BRM 51-1162 or BRL 51-1128-derived broccoli plants; and
(e) repeating the crossing and growing steps of (c) and (d) to generate further hybrid PS05151639, BRM 51-1162 or BRL 51-1128-derived broccoli plants.

21. The method of claim 19, wherein the second broccoli plant is of an inbred broccoli line.

22. The method of claim 19, comprising crossing line BRM 51-1162 with line BRL 51-1128, a sample of seed of said lines having been deposited under ATCC Accession Number PTA-9675, and ATCC Accession Number PTA-9674, respectively.

23. The method of claim 22, wherein line BRL 51-1128 is used as the male parent.

24. The method of claim 22, wherein line BRL 51-1128 is used as the female parent.

25. A plant produced by the method of claim 22.

26. A plant part of the plant of claim 25.

27. The plant part of claim 26, further defined as a leaf, a floret, a flower, a head, an ovule, pollen, or a cell.

28. A tissue culture of cells of the plant of claim 25.

29. The tissue culture of claim 28, wherein cells of the tissue culture are from a tissue selected from the group consisting of embryos, meristems, cotyledons, pollen, leaves, anthers, roots, root tips, pistil, flower, seed and stalks.

30. A broccoli plant regenerated from the tissue culture of claim 29, wherein the regenerated plant expresses all of the physiological and morphological characteristics of hybrid broccoli hybrid PS05151639.

31. A plant of broccoli line BRM 51-1162 or BRL 51-1128, a sample of seed of said lines having been deposited under ATCC Accession Number PTA-9675 and ATCC Accession Number PTA-9674, the plant further comprising a transgene.

32. A plant of broccoli line BRM 51-1162 or BRL 51-1128, a sample of seed of said lines having been deposited under ATCC Accession Number PTA-9675 and ATCC Accession Number PTA-9674, the plant further comprising a single locus conversion, wherein the conversion was introduced into said line by transformation or backcrossing.

33. A method of producing a food or feed comprising:
(a) obtaining a plant according to claim 1, wherein the plant has been cultivated to maturity; and
(b) collecting tissue from the plant.

34. The method of claim 33, wherein the plant according to claim 1 is a plant of broccoli hybrid PS05151639, a sample of seed of said hybrid PS05151639 having been deposited under ATCC Accession Number PTA-9676.

35. A method of producing broccoli seed comprising crossing the plant of claim 1 with itself or a second broccoli plant and allowing seed to form.

* * * * *